United States Patent [19]
Chen

[11] Patent Number: 5,354,281
[45] Date of Patent: Oct. 11, 1994

[54] SAFETY DISPOSABLE INFUSION SET

[76] Inventor: Shih-Shuan Chen, P.O. Box 55-1670, Taipei (104), Taiwan

[21] Appl. No.: 217,543

[22] Filed: Mar. 25, 1994

[51] Int. Cl.⁵ .................... A61M 25/02; A61M 5/32
[52] U.S. Cl. .................... 604/177; 604/165; 604/192
[58] Field of Search ............... 604/177, 165, 164, 162, 604/163, 192, 198; 128/DIG. 26

[56] References Cited

U.S. PATENT DOCUMENTS

| | | | |
|---|---|---|---|
| 3,766,915 | 10/1973 | Rychlik | 604/163 |
| 3,782,383 | 1/1974 | Thompson et al. | 604/177 |
| 4,702,735 | 10/1987 | Luther et al. | 604/165 |
| 4,834,708 | 5/1989 | Pillari | 604/165 |
| 4,888,001 | 12/1989 | Schoenberg | 604/192 |
| 4,941,881 | 7/1990 | Masters et al. | 604/162 |
| 5,112,311 | 5/1992 | Ulterberg et al. | 604/192 |
| 5,169,391 | 12/1992 | Vogel | 604/177 |
| 5,266,072 | 11/1993 | Otterberg et al. | 604/177 |
| 5,267,971 | 12/1993 | Brimhall | 604/177 |

Primary Examiner—Paul J. Hirsch

[57] ABSTRACT

A safety disposable infusion set includes: an infusion needle having a wing portion adhered onto a patient's skin such as by an adhesive tape and having a plurality of longitudinal extensions juxtapositionally formed on a bottom portion of the wing portion, and a disposal carrier having a closed sleeve for inserting a used infusion needle into the sleeve and formed on a front portion of a carrying base plate which includes a plurality of longitudinal grooves juxtapositionally recessed in the base plate for engaging the plurality of longitudinal extensions of the infusion needle, whereby upon insertion of the used infusion needle into the sleeve and upon engagement of the extensions on the needle with the grooves in the base plate, the needle will be shielded in the sleeve and also be fixedly secured on the base plate for a safety disposal.

3 Claims, 3 Drawing Sheets

SAFETY DISPOSABLE INFUSION SET

BACKGROUND OF THE INVENTION

A conventional infusion set as shown in FIG. 5 includes a needle N mounted on a holding tube T, a delivery tube D connected between the holding tube T and an infusion bottle or bag (not shown) such as filled with medical liquid or blood for intravenous injection or blood transfusion, a wing portion W disposed on two opposite side portions of the holding tube T for adhering the infusion set on a patient's skin, and a sleeve S for inserting a used needle N into the sleeve S for its safety disposal.

However, the sleeve S has a very small diameter for inserting the needle N therein and the used needle N may still stick or prick someone's hand H such as of a nurse, a doctor or a hospital housekeeper of waste disposal when inserting the needle N into the very small sleeve S as illustrated in FIG. 5.

SUMMARY OF THE INVENTION

The object of the present invention is to provide a safety disposable infusion set including: an infusion needle having a wing portion adhered onto a patient's skin such as by an adhesive tape and having a plurality of longitudinal extensions juxtapositionally formed on a bottom portion of the wing portion, and a disposal carrier having a closed sleeve for inserting a used infusion needle into the sleeve and formed on a front portion of a carrying base plate which includes a plurality of longitudinal grooves juxtapositionally recessed in the base plate for engaging the plurality of longitudinal extensions of the infusion needle, whereby upon insertion of the used infusion needle into the sleeve and upon engagement of the extensions on the needle with the grooves in the base plate, the needle will be shielded in the sleeve and also be fixedly secured on the base plate for a safety disposal.

DETAILED DESCRIPTION

Figure 1:
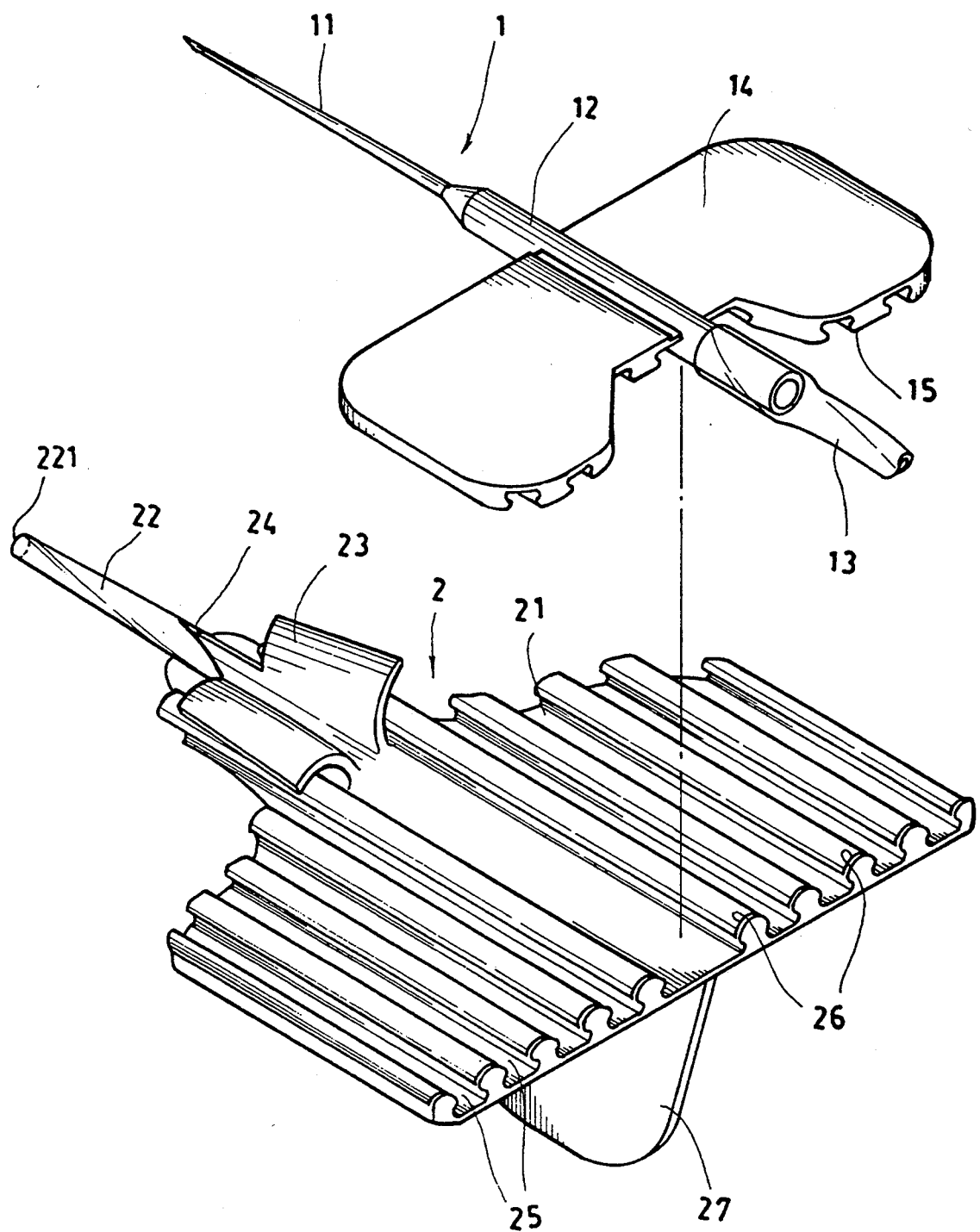
FIG. 1 is a perspective view showing two parts, an infusion needle means and a disposal carrier means, of the present invention.
Figure 2:
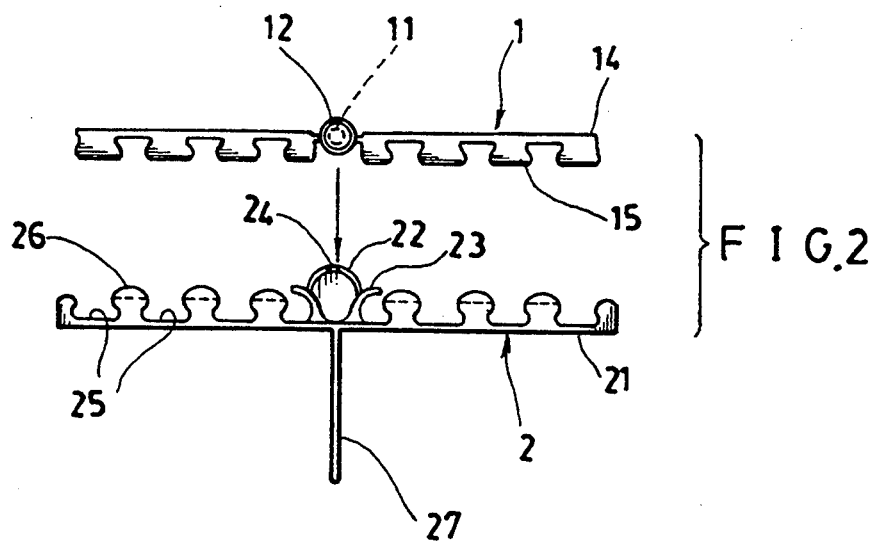
FIG. 2 is a rear view of the two parts of the present invention.
Figure 3:
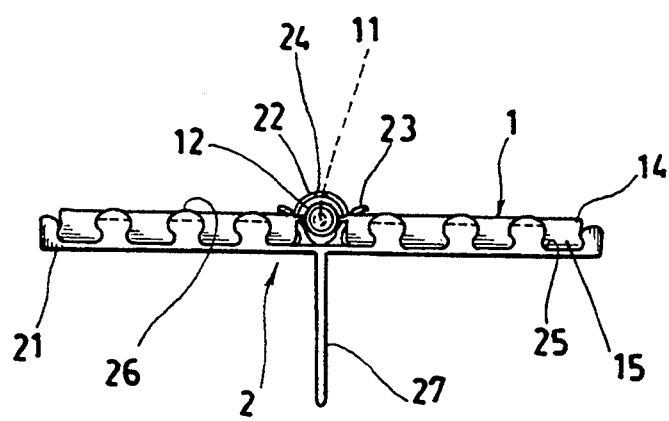
FIG. 3 is a rear view when combinably engaging the two parts of the present invention.
Figure 4:
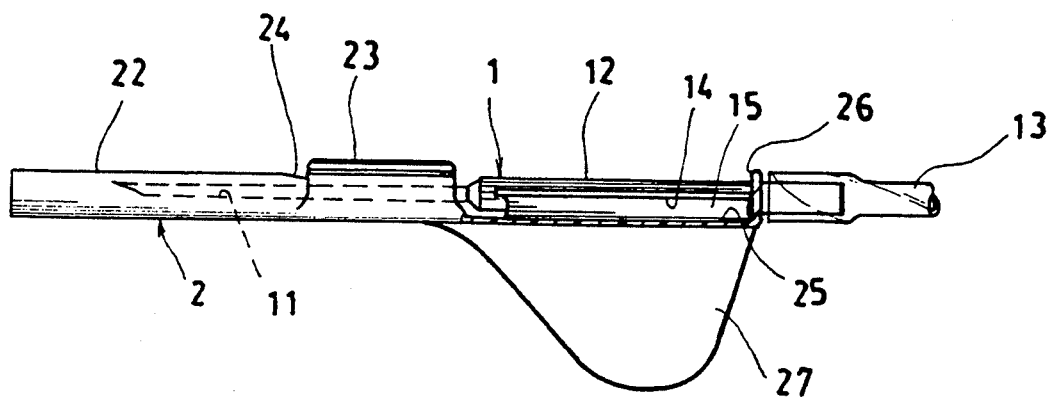
FIG. 4 is a front view illustration showing a combined two parts of the present invention convenient for their disposal.
Figure 5:
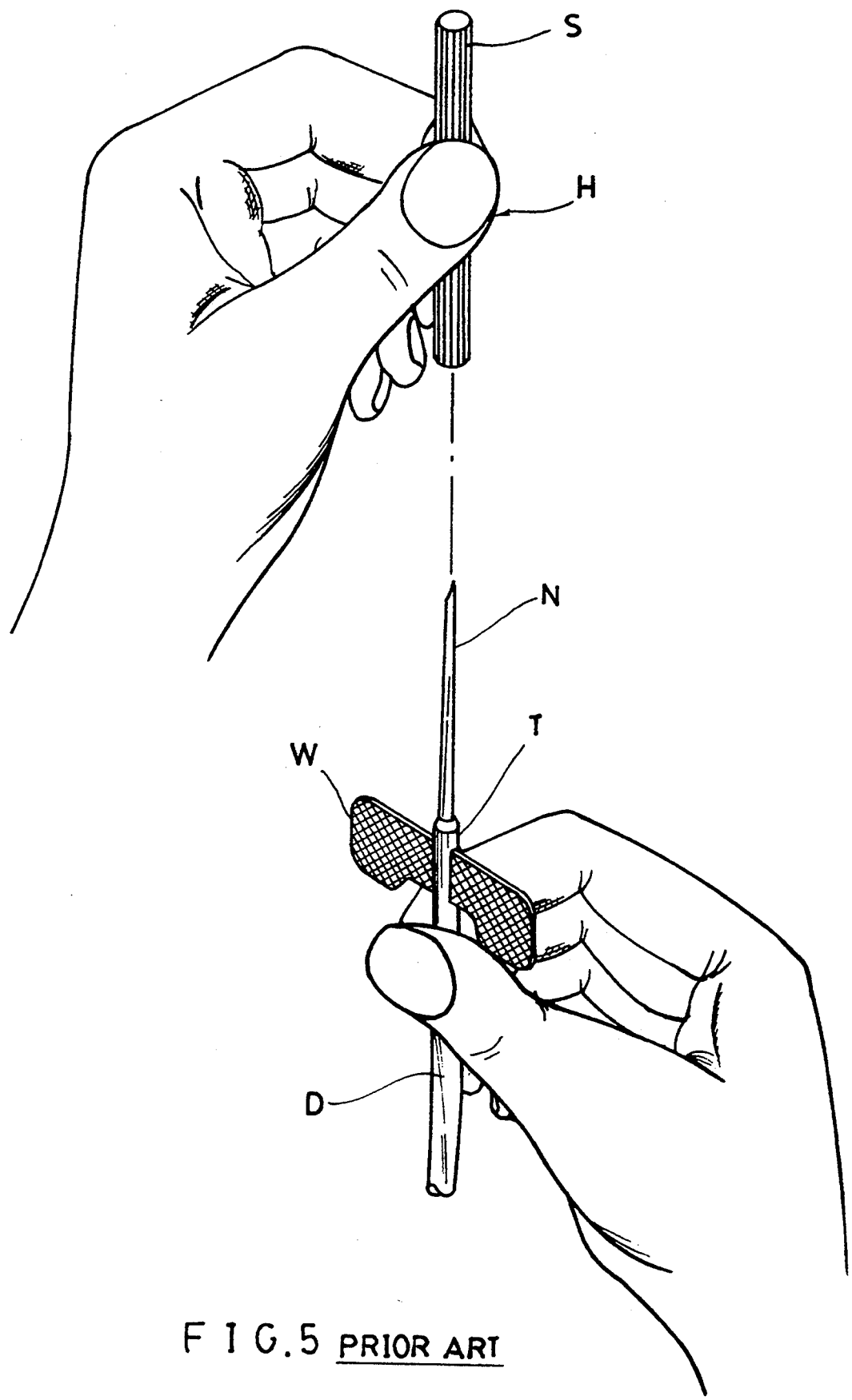
FIG. 5 shows a conventional infusion set.

As shown in FIGS. 1-4, the present invention comprises: an infusion needle means 1 and a disposal carrier means 2.

Even though the drawing figures, FIGS. 1-4, show a preferred embodiment of this invention, the shapes, designs and structures of this invention are not limited, which can be modified without departing from the spirit and scope of this invention.

The infusion needle means 1 including: a hollow needle mounted on a holding tube 12, a delivery tube 13 which may be a flexible tube connected between the needle 11 and an infusion bottle or bag filled with intravenous injection liquid or transfusion blood, a wing portion 14 disposed on two opposite sides of the holding tube 12, and a plurality of longitudinal extensions 15 juxtapositionally protruding downwardly from the wing portion 14 each longitudinal extension 15 having a cross section generally arcuate or circular shaped.

The disposal carrier means 2 includes: a carrying base plate 21, a sleeve 22 having a closed end portion 221 formed on a front end of the sleeve 22 and protruding forwardly from the base plate 21, an insertion port 24 longitudinally slotted in a rear portion of the sleeve 22 for inserting the hollow needle 11 of the infusion needle means 1 into the sleeve 22 as guided by a pair of guiding lids 23 disposed on two opposite sides of the insertion port 24 and each guiding lid 23 diverging upwardly sidewardly to form an curve guide sloping downwardly inwardly towards the insertion port 24 for easily smoothly guiding the needle 11 when used from an infusion into the sleeve 22, a plurality of longitudinal grooves 25 juxtapositionally recessed in the base plate 2 each groove 25 having a cross section of arcuate or circular shape and engageable with the plurality of longitudinal extensions 15 formed on the infusion needle means 1, and a bottom handle 27 protruding downwardly from the base plate 21 for carrying purpose.

The carrying base plate 21 of the carrier means 21 is formed with a plurality of rear blocking protrusions 26 each protrusion 26 protruding upwardly from a rear edge portion of the base plate 21 and each protrusion 26 contiguous to each longitudinal groove 25 recessed in the base plate 21, whereby upon an engagement of the needle means 1 with the carrier means 2 by engaging the longitudinal extensions 15 on the needle means 1 with the longitudinal grooves 25 in the carrier means 2 when inserting the needle 11 into the sleeve 22, the rear blocking protrusions 26 will retard a rearward retraction of the wing portion 14 of the needle means 1 to prevent a separation and release of the needle means 1 from the carrier means 2 for a safety disposal thereof.

After finishing an infusion by the needle 11 of the infusion needle means 1 of the present invention, the used needle 11 will be inserted into the sleeve 22 as guided by the guiding lid 23, and the wing portion 14 of the needle means 1 will be firmly secured onto the base plate 21 by engaging the longitudinal extensions 15 with the longitudinal grooves 25 for preventing a separation or release of the needle means 1 from the carrier means 2 and for a safety disposal of the needle means I in combination with the carrier means 2.

In inserting the needle 11 into the sleeve 22, one's left hand may hold the bottom handle 27 of the carrier means 2, while one's right hand may hold the tube 12 of the needle means 1 to insert the needle 11 into the sleeve 22 of the carrier means 2 and the wing portion 14 is then pressed downwardly to combinably engage the extensions 15 with the grooves 25 for a stable engagement and combination of the needle means ! with the carrier means 2.

Since someone's left hand holding the carrier means 2 is positioned under the base plate 21, a pricking by the needle 11 will then be eliminated to prevent infection or contamination by a used needle 11, especially for preventing hepatitis and AIDS, for hygienic and health purposes.

The combination of the needle means I with the carrier means 2 may be modified by other ways such as by hook and loop fastener, and other fastening and engaging methods, not limited in this invention.

I claim:

1. A safety disposable infusion set comprising: an infusion needle means (1) including a hollow needle mounted on a holding tube which is connected to an infusion bottle by a delivery tube, a wing portion disposed on two opposite sides of the holding tube and adapted to be adhered on a patient's skin for infusion use; and a disposal carrier means (2) including a carrying base plate securable with the wing portion of said infusion needle means, and a sleeve protruding forwardly from the base plate for inserting the hollow needle into said sleeve for shielding the needle therein for safety disposal of the needle means combined with the carrier means.

2. A safety disposal infusion set according to claim 1, wherein said infusion needle means (1) includes a plurality of longitudinal extensions (15) juxtapositionally protruding downwardly from the wing portion (14), each said longitudinal extension (15) having a cross section generally arcuate shaped; and said disposal carrier means (2) including: said carrying base plate (21) having said sleeve (22) formed with a closed end portion (21) on a front end of the sleeve (22), an insertion port (24) longitudinally slotted in a rear portion of the sleeve (22) for inserting the hollow needle (11) of the infusion needle means (1) into the sleeve (22) as guided by a pair of guiding lids (23) disposed on two opposite sides of the insertion port (24) and each said guiding lid (23) diverging upwardly sidewardly to form an curve guide sloping downwardly inwardly towards the insertion port (24) for smoothly guiding the needle (11) when used from an infusion into the sleeve (22), a plurality of longitudinal grooves (25) juxtapositionally recessed in the base plate (2) each said groove (25) having a cross section of arcuate shape and engageable with the plurality of longitudinal extensions (15) formed on the infusion needle means (1), and a bottom handle (27) protruding downwardly from the base plate (21) for carrying purpose.

3. A safety disposal infusion set according to claim 2, wherein said carrying base plate (21) of the carrier means (21) is formed with a plurality of rear blocking protrusions (26) each said protrusion (26) protruding upwardly from a rear edge portion of the base plate (21) and each said protrusion (26) contiguous to each said longitudinal groove (25) recessed in the base plate (21), whereby upon an engagement of the needle means (1) with the carrier means (2) by engaging the longitudinal extensions (15) on the needle means (1) with the longitudinal grooves (25) in the carrier means (2) when inserting the needle (11) into the sleeve (22) the rear blocking protrusions (26) will retard a rearward retraction of the wing portion (14) of the needle means (1) to prevent a separation and release of the needle means (1) from the carrier means (2) for a safety disposal thereof.

* * * * *